(12) United States Patent
Kawasaki et al.

(10) Patent No.: US 11,142,743 B2
(45) Date of Patent: Oct. 12, 2021

(54) MICROORGANISM CONTAMINATION INSPECTION SYSTEM

(71) Applicant: AIREX CO., LTD., Nagoya (JP)

(72) Inventors: Koji Kawasaki, Nagoya (JP); Haruka Hutamura, Nagoya (JP); Yukihiro Yazaki, Nagoya (JP); Zhiqiang Guo, Nagoya (JP)

(73) Assignee: AIREX CO., LTD.

( * ) Notice: Subject to any disclaimer, the term of this patent is extended or adjusted under 35 U.S.C. 154(b) by 0 days.

(21) Appl. No.: 16/096,456

(22) PCT Filed: Dec. 13, 2017

(86) PCT No.: PCT/JP2017/044754
§ 371 (c)(1),
(2) Date: Oct. 25, 2018

(87) PCT Pub. No.: WO2018/128063
PCT Pub. Date: Jul. 12, 2018

(65) Prior Publication Data
US 2019/0316074 A1    Oct. 17, 2019

(30) Foreign Application Priority Data
Jan. 6, 2017    (JP) .............................. JP2017-001006

(51) Int. Cl.
*C12M 1/34*    (2006.01)
*G01N 21/64*    (2006.01)

(52) U.S. Cl.
CPC ............. *C12M 41/36* (2013.01); *G01N 21/64* (2013.01)

(58) Field of Classification Search
CPC ......... C12M 41/36; G01N 21/64; A01N 1/02; A01N 1/0263; A01N 1/0257
(Continued)

(56) References Cited

U.S. PATENT DOCUMENTS

| 4,351,900 A | 9/1982 | Lemonnier | |
| 2013/0228498 A1* | 9/2013 | Aguero | ................... B07C 5/342 |
| | | | 209/3.1 |
| 2015/0099274 A1 | 4/2015 | Axelrod et al. | |

FOREIGN PATENT DOCUMENTS

| JP | 2009232744 | 10/2009 |
| JP | 2012233796 | 11/2012 |

(Continued)

OTHER PUBLICATIONS

Machine English Translation to JP2014081338A Description (Year: 2014).*

(Continued)

*Primary Examiner* — Michael L Hobbs
*Assistant Examiner* — Lenora A Abel
(74) *Attorney, Agent, or Firm* — Yakov Sidorin; Quarles & Brady LLP

(57) ABSTRACT

The present invention provides a microorganism inspection system that is capable of instantly inspecting individual containers for microorganism contamination of the containers that are filled with or accommodate medicines and the like. The present invention has a supply means for supplying a predetermined amount of clean air to the inside or the outer surface of a container, a collecting means for collecting the air supplied to the container by the supply means, and a detecting means for detecting microorganisms included in the air collected by the collecting means.

9 Claims, 10 Drawing Sheets

(58) Field of Classification Search
USPC .................................................. 435/287.1
See application file for complete search history.

(56) References Cited

FOREIGN PATENT DOCUMENTS

| JP | 2013170970 | | 9/2013 |
|----|------------|---|--------|
| JP | 2014081338 | | 5/2014 |
| JP | 2014081338 A | * | 5/2014 |
| WO | 2012150672 | | 11/2012 |
| WO | 2013190550 | | 12/2013 |

OTHER PUBLICATIONS

Brandvik et al. Droplet breakup in subsurface oil releases—Part 1: Experimental study of droplet breakup and effectiveness of dispersant injection, Marine Pollution Bulletin 73 (2013) 319-326 (Year: 2013).*

* cited by examiner

MICROORGANISM CONTAMINATION INSPECTION SYSTEM

CROSS-REFERENCE TO RELATED APPLICATIONS

This patent application represents the U.S. national stage entry of International Application No. PCT/JP2017/044754, filed on Dec. 13, 2017, and claims priority from Japanese Patent Application No. 2017-001006, filed on Jan. 6, 2017. The disclosure of each of the above-identified patent documents is incorporated by reference herein.

TECHNICAL FIELD

The present invention relates to a microorganism contamination inspection system for inspecting whether an inside or a surface of a container in which pharmaceuticals are filled or accommodated is contaminated by microorganisms or not.

BACKGROUND ART

Many of pharmaceuticals used in medical sites are provided in a form filled in a glass container or a plastic container. For example, liquids such as a transfusion product is filled in a plastic bottle or a plastic molded container called a soft bag and after that, it is subjected to terminal sterilization and provided to the medical site. Moreover, in a culture process of regenerative medicine, a culture tissue is accommodated in a container such as a petri dish and a tray and then, a work is carried out. The containers such as the plastic bottle, the soft bag, the petri dish, the trays and the like are represented by a "plastic bottle" in description below.

These plastic bottles are manufactured by a blow molding method of a thermoplastic resin in a container manufacturing plant and supplied to pharmaceutical filling plants and culture processes. The plastic bottle itself is made by a high-temperature molding of a hot melt resin, and sterility (ultra-low bioburden) in molding is considered to be reliable. On the other hand, a molding environment of the container manufacturing plant is generally Grade C or less, and this level is lower than Grade A which is a work environment of the pharmaceutical filling plant (Guidance on the Manufacture of Sterile Pharmaceutical Products, Ministry of Health, Labour, and Welfare), which leads to a concern on microorganism contamination to the filled products. As described above, the plastic bottles are molded/packaged under the environment at Grade C or less and after that, sterilized by an electron beam, a gamma ray, an ethylene oxide gas (EOG) and the like in a packaged state in some cases and are assembled in a pharmaceutical filling process having the concern of re-contamination in processes such as transport, removal of the packaging and the like.

On the other hand, in the pharmaceutical filing process by the terminal sterilization method, a pharmaceutical liquid is filled in the plastic bottle under the environment at Grade A or the like and subjected to sterilization in an autoclave or the like. At this time, the container or pharmaceutical product which cannot be subjected to ordinary high-temperature sterilization (121° C. or more, for example) due to an influence of heat resistance of the container or the like is called a low F0 sterile formulation, and Bioburden management for these low F0 sterile formulation can be extremely difficult. An F0 value in the low F0 sterilization is an index in pressure/heat sterilization of microorganisms and refers to an F value acquired by fixing a Z value to 10° C., and the value is frequently used for evaluation of a sterilization process.

In such pharmaceutical production process, sterility of mass-produced low F0 sterile formulation needs to be ensured. However, the plastic bottle with ultra-low Bioburden as above has gone through molding/container-packaging under the environment at Grade C and after that, through the processes of transport/removal of the packaging and the like. Therefore, it is desirable that the ultra-low Bioburden of all the plastic bottles assembled in the pharmaceutical filling process are individually inspected. If this is possible, the concern of internal microorganism contamination of the plastic bottle can be eliminated by individual management also for the low F0 sterilization formulation which employed steam sterilization lower than ordinary high-temperature sterilization (approximately 105 to 120° C., for example), which is extremely desirable in ensuring sterility of pharmaceuticals to be produced. In autoclave sterilization, batch management was carried out, and a sterility test is conducted by sampling inspection for each batch. If the result is positive in this sterility test, the batch itself is to be eliminated, which makes a great problem in yield and delivery dates.

Thus, in the following Patent Literature 1, such a sterilizing device which sterilizes entire inner and outer surfaces of a container with an electron beam irradiated from one unit of an electron beam irradiator while the container in which pharmaceuticals are filled is conveyed. According to this device, the outer surface of the container is directly sterilized by the electron beam irradiated from the electron beam irradiating device. Moreover, the inner surface of the container is sterilized by the electron beam irradiated from an outside and transmitted through the container.

Moreover, in the following Patent Literature 2, a device is proposed for sterilizing a packaging material which sterilizes the entire inner and outer surfaces of the container with the electron beam irradiated from a plurality of the electron beam irradiating devices while the container in which the pharmaceuticals are filled is conveyed. According to this device, the outer surface of the container is directly sterilized by the electron beam irradiated form each of the electron beam irradiating device. Moreover, the inner surface of the container is directly sterilized by the electron beam irradiated from a processing head (electron beam irradiation portion) inserted into the container.

CITATION LIST

Patent Literature

[Patent Literature 1] Japanese Patent Laid-Open No. 2008-56268
[Patent Literature 2] Japanese Patent Laid-Open No. 2011-514292

SUMMARY OF INVENTION

Problems to be Solved by the Invention

In the sterilizing device of the aforementioned Patent Literature 1, the electron beam irradiation device for which amounts of a device price and a maintenance cost are high is used. Moreover, in the aforementioned Patent Literature 1, the electron beam transmitted through the container is used for sterilization of the inside of the container. Thus, irradiation intensity of the electron beam of the outer surface is different from that of the inner surface, and excessive electron beams need to be irradiated to the outer surface in order to sufficiently sterilize the inner surface, which leads to a concern of deterioration and discoloration of the container itself in the blow-molded plastic bottle. Moreover, there is a concern that radicals are generated in polymers of the container, which influences the product.

On the other hand, in the device for sterilization in the aforementioned Patent Literature 2, the electron beam irradiating devices for which the amounts of the device price and the maintenance cost are high are used in plural similarly to the aforementioned Patent Literature 1. Moreover, in the aforementioned Patent Literature 2, the special processing head needs to be inserted into the container for sterilization of the inside of the container, and a structure of the device becomes complicated. Furthermore, in the aforementioned Patent Literature 2, too, deterioration of the container itself by the electron beam is concerned about in the blow-molded plastic bottle similarly to the aforementioned Patent Literature 1.

Moreover, the low F0 sterile formulation using the plastic bottle is produced in a large quantity, and sterilization of all the plastic bottles in the pharmaceutical filling process has a problem in a point of productivity. Moreover, sterility at molding of the plastic bottle itself (ultra-low Bioburden) is at a reliable level as described above, and a price of the plastic bottle itself is low. Therefore, if there is a method of eliminating a small quantity of plastic bottles about which internal microorganism contamination from the large quantity of plastic bottles is concerned, sterility of the low F0 sterile formulation is highly ensured.

Thus, the present invention has an object to solve the aforementioned problems and to provide a microorganism contamination inspection system which can instantaneously inspect microorganism contamination of individual containers in which the pharmaceuticals are filled or accommodated.

Means for Solving the Problems

In solving the aforementioned problems, the inventors, as the result of keen study, collected microorganisms adhering to the container surface by blowing clean air, found that the collected microorganism in the air could be instantaneously detected by a microorganism detector and completed the present invention.

That is, the microorganism contamination inspection system according to the present invention (A1 to A4) is, according to description in claim 1, an inspection system for inspecting microorganism contamination on an inside or on a surface of a container (B), characterized by including:

supply means (10) for supplying a predetermined amount of clean air to the inside or the surface of the container;

collecting means (20) for collecting the air supplied into the container by the supply means; and detecting means (30) for detecting the microorganism contained in the air collected by the collecting means.

Moreover, the present invention is the microorganism contamination inspection system described in claim 1, according to claim 2, characterized in that the supply means has an air supply device (11), a sterile filter (12), clean air supply line (13), and an ejection nozzle (14), the air supplied from the air supply device is sterilized/cleaned in the sterile filter, and the sterilized/cleaned air is ejected as clean air to an inside or a surface of the container which is an inspection target from the ejection nozzle through the clean air supply line; and the collecting means has an air suctioning device (21a, 21b), an inspection air supply line (22a, 22b), and a collector (23), collects the air ejected into the inside or the surface of the container which is an inspection target by the collector, and supplies the collected air as an inspection air to the detecting means through the inspection air supply line.

Moreover, the present invention is the microorganism contamination inspection system described in claim 1 or 2, according to the description in claim 3, characterized in that the detecting means has a microorganism detection portion (32); and in the microorganism detection portion, the number of microorganism particles in the inspection air is instantaneously detected.

Moreover, the present invention is the microorganism contamination inspection system described in claim 1 or 2, according to the description in claim 4, characterized in that the detecting means has a particle detection portion (31) and a microorganism detection portion (32); and by instantaneously detecting the total number of the microorganism particles and non-microorganism particles in the inspection air in the particle detection portion; and by instantaneously detecting the number of microorganism particles in the inspection air in the microorganism detection portion, the number of microorganism particles is instantaneously detected by discriminating the microorganism particles from the non-microorganism particles in the inspection air.

Moreover, the present invention is the microorganism contamination inspection system described in claim 3 or 4, according to the description in claim 5, characterized in that the microorganism detection portion instantaneously detects the number microorganism particles in the inspection air by a laser induced fluorescence method.

Advantageous Effect of the Invention

According to the configuration of the aforementioned claim 1, the microorganism contamination inspection system according to the present invention has the supply means, the collecting means, and the detecting means. The supply means supplies a predetermined amount of the clean air to the inside or the surface of the container. Subsequently, the collecting means collects the air supplied into the container by the supply means. Subsequently, the detecting means detects the microorganism contained in the air collected by the collecting means.

As described above, the particles adhering to the inside or the surface of the container are captured by the clean air supplied by the supply means. The clean air having captured the particles is collected by the collecting means and supplied to the detecting means. If the particles captured by the clean air are caused by the microorganism, they are instantaneously detected by the detecting means. Thus, according to the configuration of the aforementioned claim. 1, the microorganism contamination inspection system which can instantaneously inspect the microorganism contamination of the container in which the pharmaceuticals are filled or accommodated can be provided for the individual containers.

Moreover, according to the configuration of the aforementioned claim 2, the supply means has the air supply device, the sterile filter, the clean air supply line, and the ejection nozzle. The air supplied from the air supply device is sterilized/cleaned in the sterile filter to the clean air. This clean air is ejected into the inside or the surface of the container which is the inspection target from the ejection nozzle through the clean air supply line. As a result, the particles adhering to the inside or the surface of the container is captured by the clean air.

On the other hand, the collecting means has the air suctioning device, the inspection air supply line, and the collector. The air suctioning device collects the air capturing the particles from the collector. This collected air is supplied to the detecting means as the inspection air through the inspection air supply line. Thus, according to the configuration of the aforementioned claim 2, the effect similar to that of claim 1 can be exerted more specifically.

Moreover, according to the configuration of the aforementioned claim 3, the detecting means has the microorganism detection portion. In this microorganism detection portion, if the particles in the inspection air are caused by the microorganism, the number of the microorganism particles is instantaneously detected. Thus, according to the configuration of the aforementioned claim 3, the effect similar to that of claim 1 or 2 can be exerted more specifically.

Moreover, according to the configuration of the aforementioned claim 4, the detecting means has the particle detection portion and the microorganism detection portion. In the particle detection portion, the total number of the microorganism particles and the non-microorganism particles in the inspection air is instantaneously detected. Moreover, in the microorganism detection portion, the microorganism particles and the non-microorganism particles are discriminated in the particles in the inspection air, and the number of the microorganism particles caused by the microorganism is instantaneously detected. Thus, according to the configuration of the aforementioned claim 4, the effect similar to that of claim 1 or 2 can be exerted more specifically, and the total number of the microorganism particles and non-microorganism particles can be also inspected.

Moreover, according to the configuration of the aforementioned claim 5, the microorganism detection portion instantaneously detects the number of the microorganism particles in the inspection air by the laser induced fluorescence method. Thus, according to the configuration of the aforementioned claim. 5, the effect similar to that of claim 3 or 4 can be exerted more specifically.

MODE FOR CARRYING OUT THE INVENTION

First Embodiment

A microorganism contamination inspection system according to the present invention will be described below by referring to each of the embodiments. First, in a first embodiment, a plastic bottle having a capacity of 150 ml is used as a container in which a pharmaceutical to be inspected is filled. The plastic bottle used in this first embodiment is a plastic container obtained by molding a thermoplastic resin by a blow molding method. The thermoplastic resin is not particularly limited but polyethylene, polypropylene, nylon, polyester and other resins can be used.

In the present invention, the container to be inspected is not limited to a container in which the pharmaceuticals are filled but all the containers such as a container in which food is filled, requiring inspection of microorganism contamination can be made targets. Moreover, not only the plastic bottle but also glass bottles or cans can be also made a target. Furthermore, not only the bottles but also soft bags, petri dishes, trays, films and the like can be also made targets.

Figure 1:
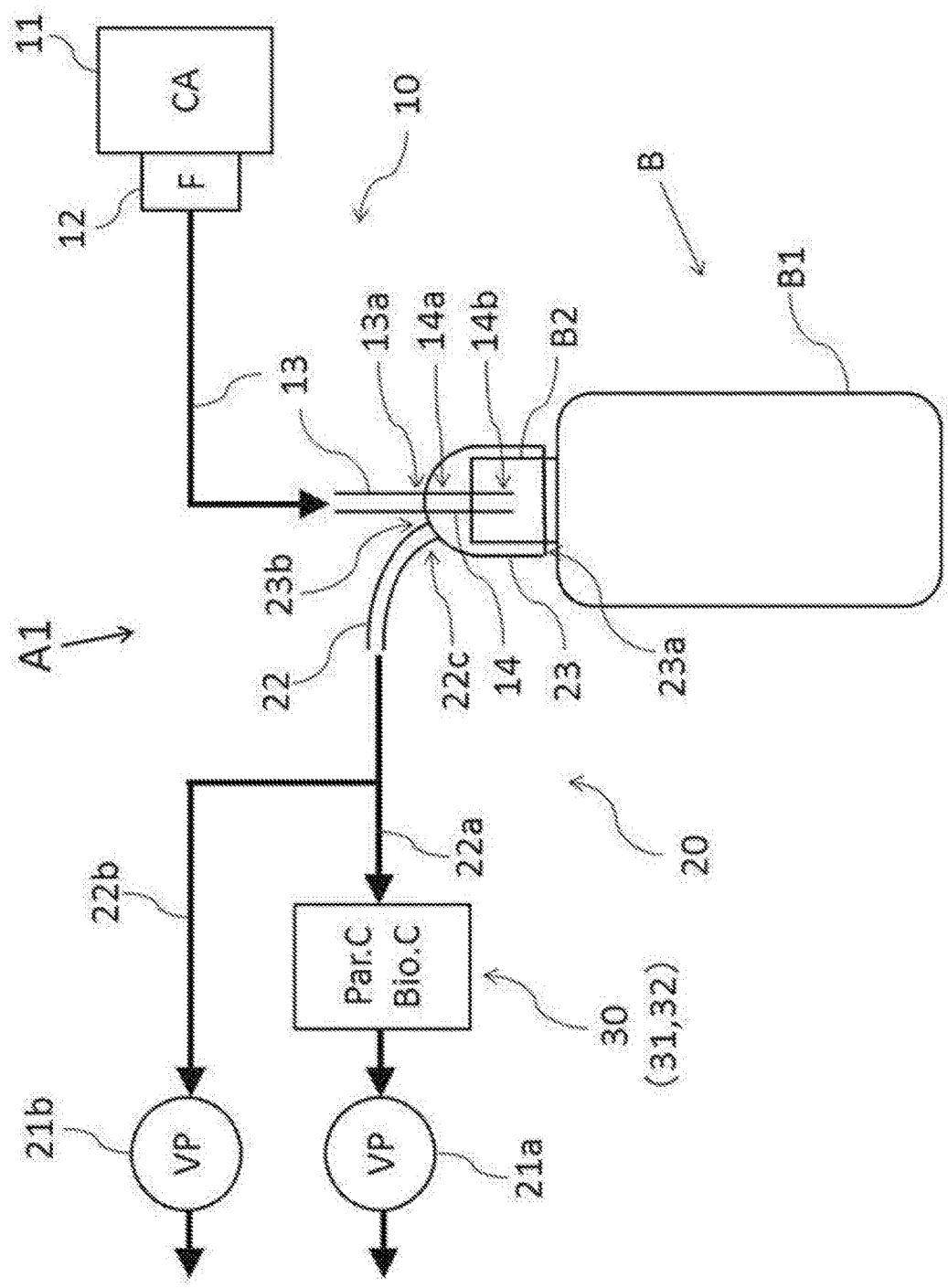
FIG. 1 is a schematic diagram illustrating configuration of a microorganism contamination inspection system according to a first embodiment.

Subsequently, the microorganism contamination inspection system according to this first embodiment will be described in accordance with the drawings. FIG. 1 is a schematic diagram illustrating configuration of the microorganism contamination inspection system according to this first embodiment. FIG. 1 illustrates a state where a plastic bottle to be inspected is attached to the microorganism contamination inspection system. Moreover, though not shown, the microorganism contamination inspection system in FIG. 1 is accommodated in a clean room, a RABS (Restricted Access Barrier System) or an isolator under an environment at Grade A.

As illustrated in FIG. 1, the microorganism contamination inspection system A1 according to this first embodiment has a supply device 10 for supplying air into the plastic bottle B, a collecting device 20 for collecting the air in the plastic bottle B, and a detecting device 30 for detecting particles floating in the air collected by the collecting device 20 and microorganism particles in it. In this first embodiment, the plastic bottle B is a narrow-mouth bottle made of a body portion B1 and a mouth portion B2 as illustrated in FIG. 1 and is attached to a microorganism contamination inspection system A1 in an upright state (in a state where the mouth portion B2 is opened upward).

In FIG. 1, the supply device 10 includes a compressor 11, a sterile filter 12, a supply pipeline 13, and an ejection nozzle 14. The compressor 11 compresses the air into a compressed air. The compressor 11 may include an after cooler, a receiver tank, a dryer, an air filter, a pressure switch, an electromagnetic valve and the like in addition to the sterile filter 12.

The sterile filter 12 sterilizes/cleans the compressed air supplied from the compressor 11 into clean air at Grade A. A type of the sterile filter 12 is not particularly limited but an ordinary HEPA filter or the like can be used. The clean air having passed through the sterile filter 12 is sent to the ejection nozzle 14 through the supply pipeline 13. One end portion 13a of the supply pipeline 13 and one end portion 14a of the ejection nozzle 14 communicate with each other and they are integrally connected to a collector 23 (which will be described later) at this communication portion.

In FIG. 1, the collecting device 20 includes two units of suctioning pumps 21a and 21b, a suctioning pipeline 22 (22a, 22b), and the collector 23. The suctioning pumps 21a and 21b suction and collect the air from the collector 23 through the suctioning pipeline 22. The air collected from this collector 23 corresponds to an air ejected from the aforementioned ejection nozzle 14 into the plastic bottle B and flowing out of the mouth portion B2 of the plastic bottle B. Therefore, this air is an inspection air for inspecting the particles adhering to the inside of the plastic bottle B.

The suctioning pump 21a in the two units of the suctioning pumps is a suctioning pump connected to a detecting device 30 (which will be described later) and suctions an amount to be supplied to the detecting device 30 in the inspection air suctioned from the collector 23. The amount of the inspection air to be supplied to the detecting device 30 only needs to be adjusted as appropriate depending on the capacity of the plastic bottle B, an amount of the clean air ejected into the plastic bottle B, and a structure of the detecting device 30. In this first embodiment, it was set to 0.1 to 1.0 cft/min (cubic feed/minute). On the other hand, the suctioning pump 21b is a suctioning pump for main air-discharge, and the remaining inspection air excluding the amount to be supplied by the suctioning pump 21a to the detecting device 30 in the inspection air suctioned from the collector 23 is discharged to an outside of a work environment.

One end portion 22c of the suctioning pipeline 22 communicates with an inside of the collector 23 and is integrally connected to the collector 23 at this communication portion. Moreover, the suctioning pipeline 22 branches in the middle into two suctioning pipelines 22a and 22b. One suctioning pipeline 22a is a pipeline for inspection and is connected to the suctioning pump 21a through the detecting device 30. The other suctioning pipeline 22b is a pipeline for main air-discharge and is connected to the suctioning pump 21b.

Here, the structure of the collector 23 will be described. The collector 23 has a shape and a size that can cover the mouth portion B2 of the plastic bottle B. It is preferable that the collector according to the present invention sufficiently covers a portion where the clean air is ejected in the container to be inspected. Therefore, if the inspection target is a plastic bottle, it has a shape that can cover the mouth portion thereof. Moreover, if the inspection target is a petri dish or a tray, it has a shape that can cover its inner surface (surface to be used). In this first embodiment, since the inspection target is a plastic bottle, the collector 23 is a semispherical container with an end surface 23a open. A length and a diameter of the collector 23 are sizes that cover and shield most of the mouth portion B2 of the plastic bottle B and are attached so that most of the open mouth portion B2 of the plastic bottle B is accommodated inside the semi-sphere of the collector 23 as illustrated in FIG. 1.

On the other hand, a semispherical end portion 23b of the collector 23 is closed. To this end portion 23b, the end portion 13a of the aforementioned supply pipeline 13 and the end portion 14a of the ejection nozzle 14 are integrally connected in a communicating state. Moreover, the one end portion 22c of the suctioning pipeline 22 is integrally connected in a state communicating with the inside of the collector 23. Moreover, the other end portion 14b of the ejection nozzle 14 is an ejection port of the clean air and is inserted into a vicinity of the mouth portion B2 of the plastic bottle B as illustrated in FIG. 1.

Figure 2:
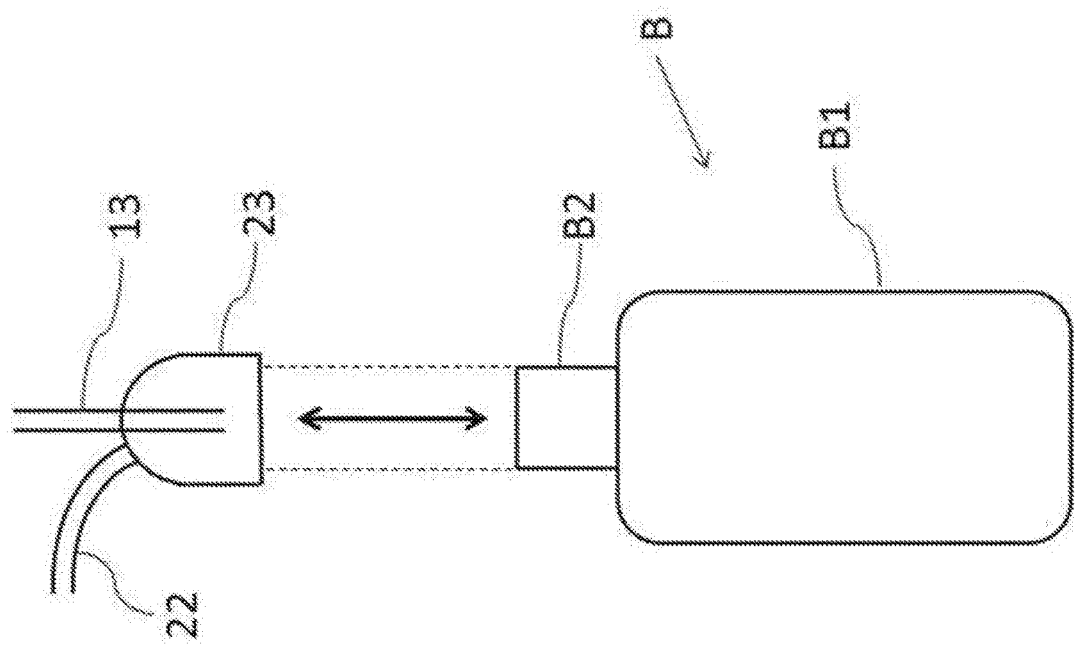
FIG. 2 is a schematic diagram illustrating a state where a plastic bottle is attached to/detached from the microorganism contamination inspection system in the configuration diagram of FIG. 1.

Here, attachment of the plastic bottle B to the microorganism contamination inspection system A1 will be described. FIG. 2 is a schematic diagram illustrating a state where the plastic bottle B is attached to/detached from the microorganism contamination inspection system according to this first embodiment. As illustrated in FIG. 2, the plastic bottle B is at an attachment position to the microorganism contamination inspection system A1 through an automatic running device (or may be manually). In this state, the plastic bottle B before the inspection is attached so that the open mouth portion B2 of the plastic bottle B is accommodated inside the semi-sphere of the collector 23 by the vertical movement of the collector 23 or the vertical movement of the plastic bottle B. Moreover, with regard to the plastic bottle B after the inspection is finished, the open mouth portion B2 of the plastic bottle B is removed from the inside of the semi-sphere of the collector 23 similarly by the vertical movement of the collector 23 or the vertical movement of the plastic bottle B.

Subsequently, the detecting device 30 will be described. In FIG. 1, the detecting device 30 includes a particle counter 31 and a floating bacteria counter 32. These counters 31 and 32 suction a certain amount of the inspection air sent from the suctioning pipeline 22 as a sample from a collecting port and detect the particle (particles) and floating bacteria (microorganism particles) in that by an optical measuring instrument or the like. Particularly in recent years, the floating bacteria counter using the optical measuring instrument can drastically improve work efficiency as a Rapid Microbiological Method (RMM) that can instantaneously discriminate particles originated from the microorganism as compared with conventional culture methods.

Any method may be employed for the particle counter 31, but in this first embodiment, a particle counter using grain size sorting by a light scattering method was employed for the purpose of rapid inspection. If a particle adheres to the inside of the plastic bottle B in the inspection by this particle counter 31, it has been peeled off and is floating in the inspection air, and this can be detected. As described above, the particle counter 31 can instantaneously detect the total number of the microorganism particles and non-microorganism particles in the inspection air.

On the other hand, though any method may be employed for the floating bacteria counter 32, a floating bacteria counter using fluorescence identification by a laser induced fluorescence method was employed for the purpose of the rapid inspection in this first embodiment. The laser induced fluorescence method uses a fact that a particle related to microorganism or cell viability in the particles floating in the inspection air emits fluorescence when it is induced by ultraviolet rays. If the particle adheres to the inside of the plastic bottle B in the inspection by this floating bacteria counter 32, it has been peeled off and is floating in the inspection air, and this can be detected.

As described above, the floating bacteria counter 32 can instantaneously detect the number of microorganism particles in the total number of the microorganism particles and the non-microorganism particles in the inspection air detected by the particle counter 31.

As described above, in this first embodiment, by employing the particle counter 31 and the floating bacteria counter 32, if a particle adheres to the inside of the plastic bottle B, the total number of the particles is detected, the microorganism particles and the non-microorganism particles are discriminated, and the number of the microorganism particles can be instantaneously detected.

Here, the microorganism particles which can be detected by the floating bacteria counter 32 according to this first embodiment will be described. Since the floating bacteria counter 32 employs the laser induced fluorescence method, the particles induced by the ultraviolet rays and emitting fluorescence in the particles (particles) detected by the particle counter 31 are detected as microorganism particles (also referred to as floating bacteria). These particles emitting fluorescence include not only existing microorganisms but also all the particles originated from microorganisms such as remains of the microorganisms. Moreover, though it is extremely rare, there is a possibility that the non-microorganism particles induced by the ultraviolet rays and emitting fluorescence are detected. In ensuring the sterility of the low F0 sterile formulation which is the object of the present invention, existing microorganisms are targeted but by detecting all the particles originated from the microorganisms in a wide meaning, safety against microorganisms contamination is further improved, which is preferable in ensuring sterility of pharmaceuticals to be produced.

Subsequently, an operation of the microorganism contamination inspection system according to this first embodiment will be described. In this first embodiment, the collector 23 and the plastic bottle B of the microorganism contamination inspection system A1 are both molded by transparent plastic and in FIG. 1, each of them is described in a state seen through the inside. In FIG. 1, the mouth portion B2 of the plastic bottle B is accommodated inside the collector 23 of the microorganism contamination inspection system A1. Moreover, in the vicinity of the mouth portion B2 of the plastic bottle B, the end portion 14b which is an ejection port of the ejection nozzle 14 is inserted toward the inside.

In this state, the compressor 11 is operated. As a result, the clean air (compressed air) supplied from the compressor 11 and having passed through the sterile filter 12 is ejected to the whole surface of the inside of the body portion B1 of the plastic bottle B from the end portion 14b which is the ejection port of the ejection nozzle 14 through the supply pipeline 13 and the ejection nozzle 14.

As a result, if the particle adheres to the inside of the plastic bottle B, this particle is blown out by energy of the ejected clean air (compressed air), scattered inside the plastic bottle B and floated. An ejection amount and an ejection pressure of the clean air (compressed air) ejected into the inside of the plastic bottle B are not particularly limited but only need to be set as appropriate in accordance with a shape and a capacity of the plastic bottle B. In this first embodiment, when the ejection pressure of the clean air (compressed air) is 0.1 to 1.0 MPa, the ejection amount is 0.1 to 1.0 L/min or preferably 0.2 to 0.5 L/min. As a result, the air in the container is completely replaced by the ejected clean air. Moreover, by adjusting the ejection amount, the number of replacement can be ensured at several times to several tens times, and collection of the particles adhering to the inside of the plastic bottle B can be made more reliable.

The ejection of the clean air (compressed air) to the inside of the container is employed in a process of air washing also in the ordinary pharmaceutical filling process in some cases. This air washing is an operation for eliminating foreign substances adhering to the inside of the container but inspection of microorganism contamination from this air is not carried out. Therefore, the microorganism contamination inspection system according to the present invention can configure more rational pharmaceutical filling process by being included in this air washing and operated or by being operating together with the air washing.

In conjunction with the ejection of the clean air (compressed air) into the inside of this plastic bottle B, the suctioning pumps 21a and 21b are operated. It is preferable that all the inspection air (containing the scattered floating particles) ejected into the inside of the plastic bottle B and flowing out of the mouth portion B2 is collected by the collector 23 by means of the operation of the suctioning pumps 21a and 21b. That is because, if the amount of the inspection air collected from the collector 23 is smaller than the amount of the clean air ejected into the inside of the plastic bottle B, there is a concern that a part of the inspection air (containing the scattered floating particles) flowing out of the mouth portion B2 of the plastic bottle B contaminates the work environment (at Grade A).

A part of the inspection air collected from the collector 23 is supplied to the detecting device 30 through the suctioning pipeline 22a in order to detect the total number of the particles (particles) and the number of floating bacteria (microorganism particles), and after that, it is discharged to the outside of the work environment through the suctioning pump 21a. Moreover, the remaining inspection air collected from the collector 23 is discharged to the outside of the work environment through the suctioning pump 21b through the suctioning pipeline 22b. It may be so controlled that in this first embodiment that the suctioning pump 21b is operated at all times, while the suctioning pump 21a is operated in conjunction only when the compressor 11 is operated.

In this first embodiment, a part of the inspection air supplied to the detecting device 30 is inspected by the particle counter 31 and the floating bacteria counter 32. The inspection result is detected as the total number of the particles (microorganism particles and non-microorganism particles) and the number of floating bacteria (microorganism particles) and displayed as a detected particle number (particles/second) to elapsed time (seconds). In this first embodiment, inspection can be completed in several to several tens seconds for one plastic bottle B, and it does not give any influence to productivity of the filling process even if it is included inline in the pharmaceutical filling process.

Subsequently, a check test was conducted in order to check performances of the microorganism contamination inspection system according to this first embodiment. Hereinafter, a method of the check test will be described. In the check test, the microorganism contamination inspection system A1 illustrated in FIG. 1 is installed in an isolator under an environment at Grade A. As an inspection target, a plurality of plastic bottles (same as the plastic bottle B) for which no microorganism contamination was checked in advance was prepared, and they were divided into four groups, that is, X1, X2, X3, and X4.

Subsequently, riboflavin powders as simulated contaminant of the microorganism particles and lactose powders as simulated contaminant of the non-microorganism particles were prepared. The riboflavin powders as the simulated substance of the microorganism particles showed a fluorescent reaction. On the other hand, the lactose powders as the simulated substance of the non-microorganism particles did not show the fluorescent reaction.

Here, into the plastic bottle X1, the simulated contaminant was not input as a blank sample (non-contaminated). Into the plastic bottle X2, 0.5 mg of riboflavin powders and 0.5 mg of lactose powders were input as a contaminated sample. Into the plastic bottle X3, 1.0 mg of riboflavin powders and 1.0 mg of lactose powders were input as a contaminated sample. Into the plastic bottle X4, 1.5 mg of riboflavin powders and 1.5 mg of lactose powders were input as a contaminated sample.

Figure 3:
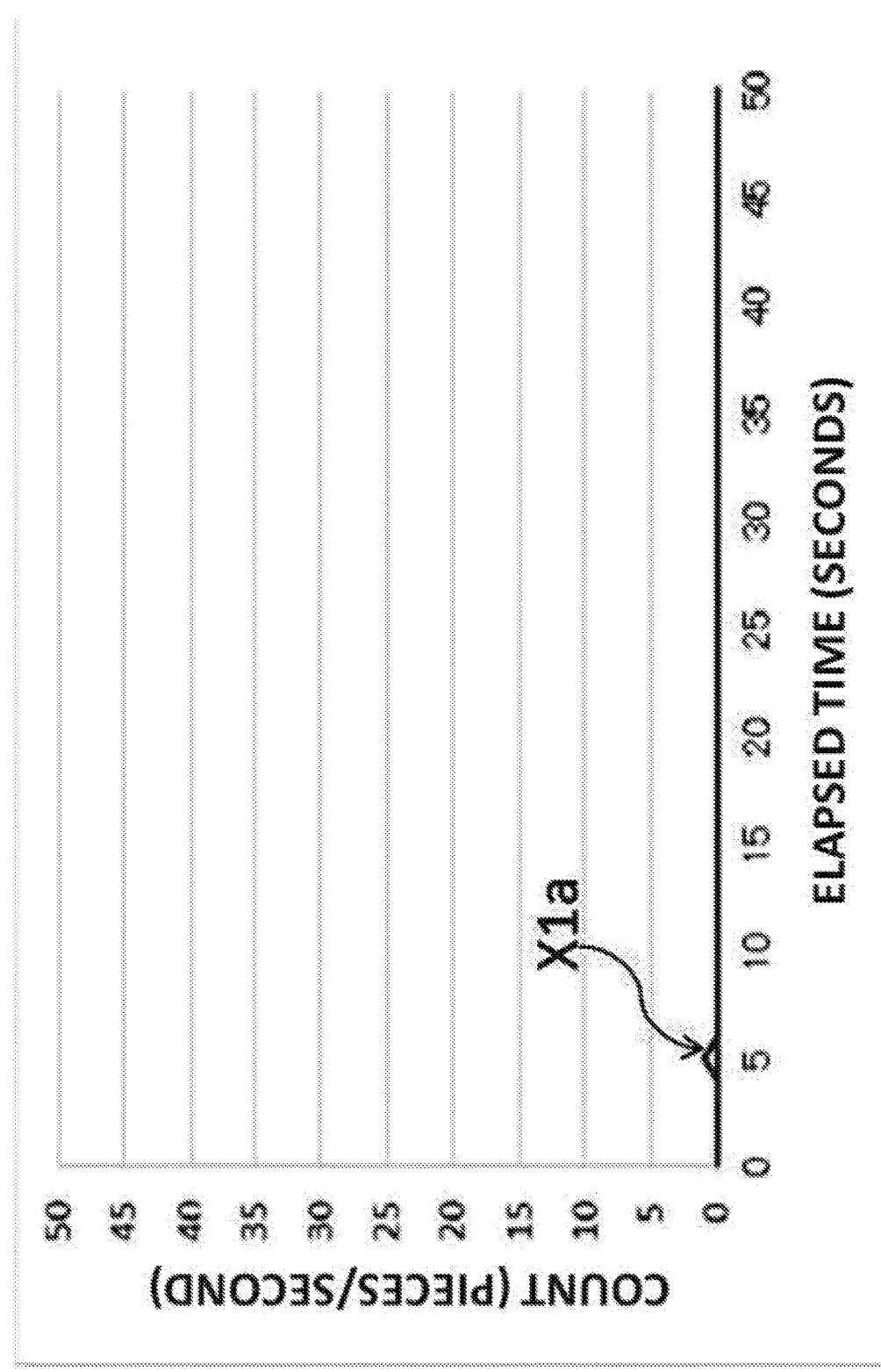
FIG. 3 is a graph illustrating an inspection result of a plastic bottle X1 (non-contaminated sample) in a check test.
Figure 4:
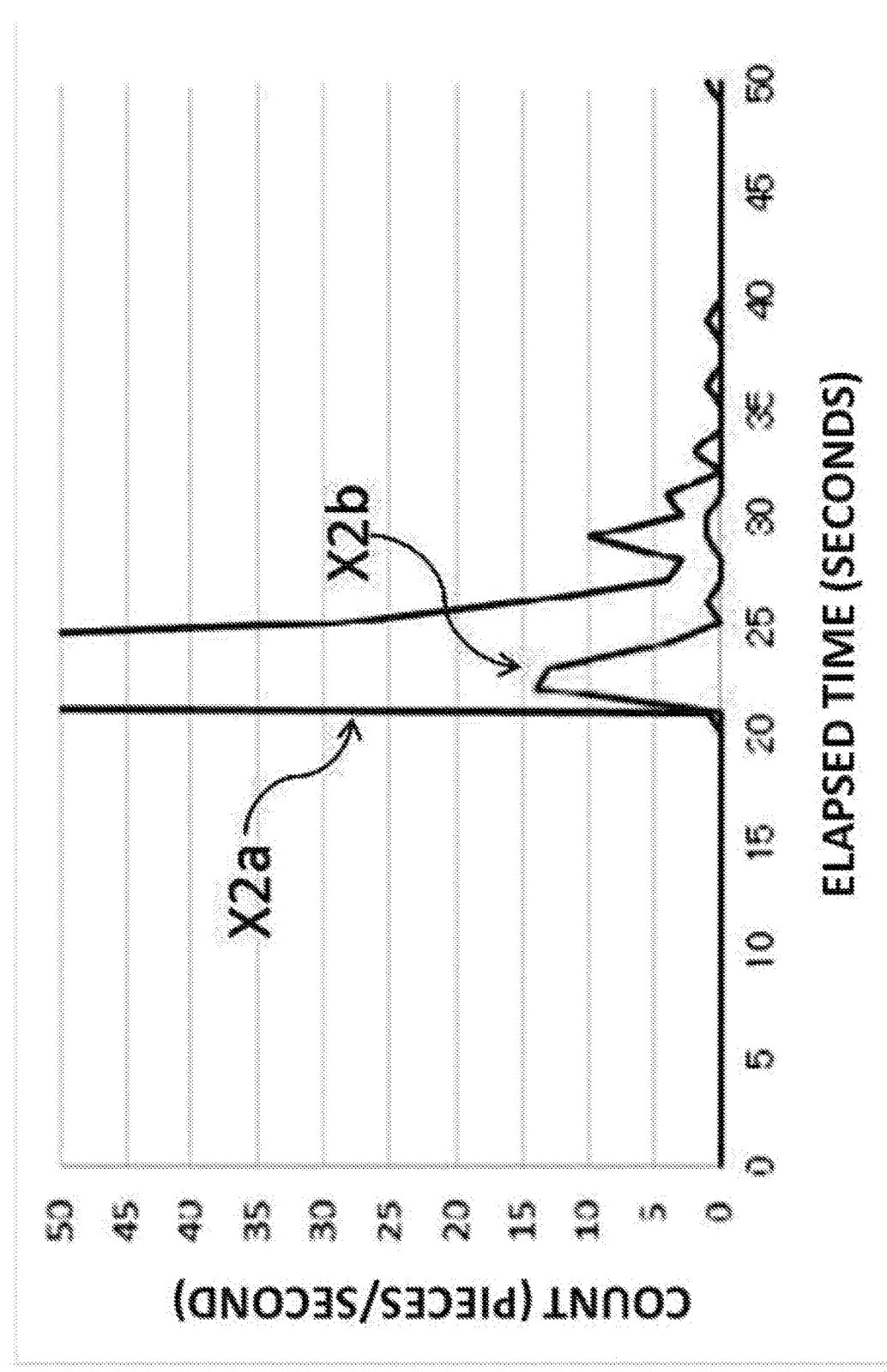
FIG. 4 is a graph illustrating an inspection result of a plastic bottle X2 (contaminated sample) in the check test.
Figure 5:
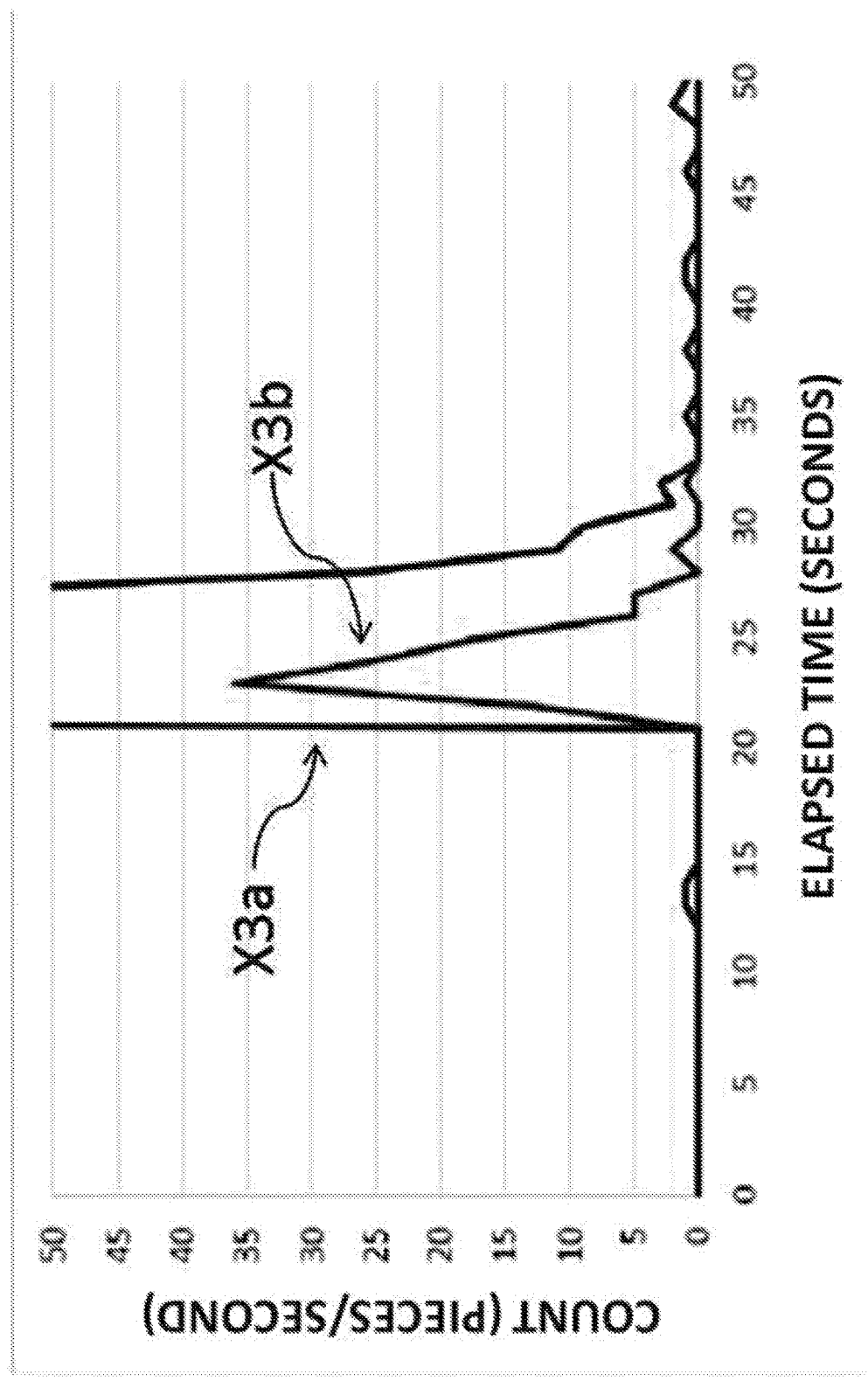
FIG. 5 is a graph illustrating an inspection result of a plastic bottle X3 (contaminated sample) in the check test.
Figure 6:
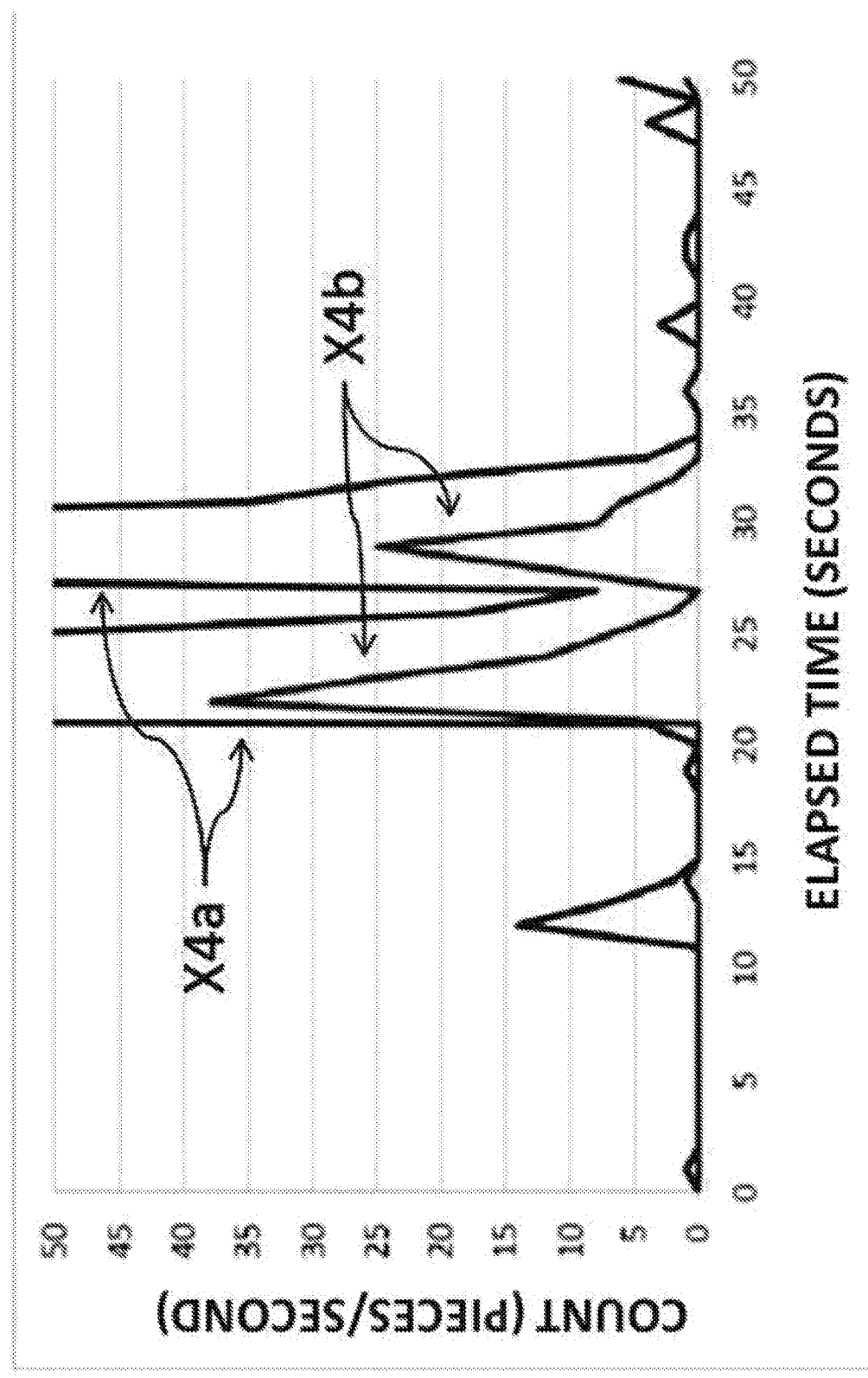
FIG. 6 is a graph illustrating an inspection result of a plastic bottle X4 (contaminated sample) in the check test.

Subsequently, inspection was conducted for each of the plastic bottles X1 to X4 by using the microorganism contamination inspection system A1. Graphs of the inspection result are shown in FIGS. 3 to 6. FIG. 3 is a graph illustrating the inspection result of the plastic bottle X1 (non-contaminated sample) in the check test. FIG. 4 is a graph illustrating the inspection result of the plastic bottle X2 (non-contaminated sample) in the check test. FIG. 5 is a graph illustrating the inspection result of the plastic bottle X3 (contaminated sample) in the check test. FIG. 6 is a graph illustrating the inspection result of the plastic bottle X4 (contaminated sample) in the check test. Moreover, in FIGS. 3 to 6, a vertical axis indicates a count number (pieces/second) of the particles, and a lateral axis indicates an elapsed time (seconds).

In FIG. 3 illustrating the inspection result of the plastic bottle X1 (non-contaminated sample) by the particle counter 31, a detection peak X1a of the particles (riboflavin and lactose) was slightly found. However, since the plastic bottle X1 is a blank test (non-contaminated), this detection is considered to be made by particles other than riboflavin and lactose. On the other hand, detection of the simulated floating bacteria (riboflavin) by the floating bacteria counter 32 was not found. Therefore, the detection peak X1a of the detected particles is not contamination caused by the microorganisms.

In FIG. 4 illustrating the inspection result of the plastic bottle X2 (contaminated sample), a detection peak X2a of the particles (riboflavin and lactose) by the particle counter 31 was largely found. On the other hand, a detection peak X2b of the simulated floating bacteria (riboflavin) by the floating bacteria counter 32 was also found. The count number of the simulated floating bacteria (riboflavin) is smaller than the count number of the particles, and it was found that riboflavin and lactose are clearly discriminated.

In FIG. 5 illustrating the inspection result of the plastic bottle X3 (contaminated sample), a detection peak X3a of the particles (riboflavin and lactose) by the particle counter 31 was largely found. On the other hand, a detection peak X3b of the simulated floating bacteria (riboflavin) by the floating bacteria counter 32 was also found. The count number of the simulated floating bacteria (riboflavin) is smaller than the count number of the particles, and it was found that riboflavin and lactose are clearly discriminated. Moreover, the count number (detection peak X3b in FIG. 5) of the simulated floating bacteria (riboflavin) is larger than the count number (detection peak X2b in FIG. 4) of the simulated floating bacteria (riboflavin) in the aforementioned plastic bottle X2.

In FIG. 6 illustrating the inspection result of the plastic bottle X4 (contaminated sample), two separate detection peaks X4a of the particles (riboflavin and lactose) by the particle counter 31 were largely found. On the other hand, two separate detection peaks X4b of the simulated floating bacteria (riboflavin) by the floating bacteria counter 32 were also found. The count number of the simulated floating bacteria (riboflavin) is smaller than the count number of the particles, and it was found that riboflavin and lactose are clearly discriminated. Moreover, the count number (detection peak X4b in FIG. 6) of the simulated floating bacteria is larger than the count number (detection peak X3b in FIG. 5) of the simulated floating bacteria (riboflavin) in the aforementioned plastic bottle X3.

Figure 7:
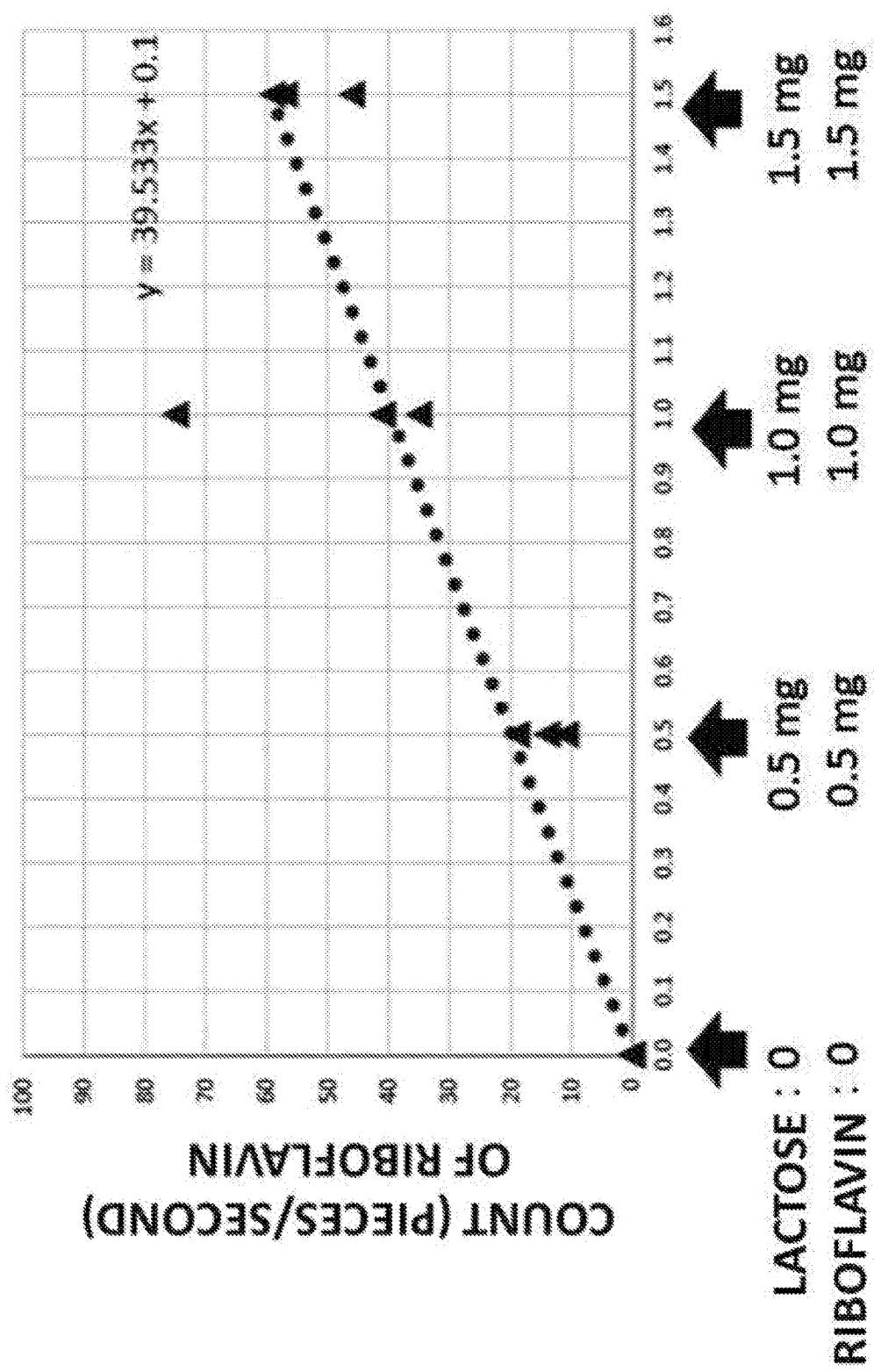
FIG. 7 is a graph indicating a count number of simulated floating bacteria (riboflavin) to an input amount of a simulated contaminant in the check test.

Thus, the detection results (FIGS. 3 to 6) of the simulated floating bacteria (riboflavin) in the plastic bottles X1 to X4 were examined. FIG. 7 is a graph showing the count number of the simulated floating bacteria (riboflavin) to the input amount of the simulated contaminant in the check test. In FIG. 7, the count number of riboflavin by the floating bacteria counter 32 is accurately proportional to the input amount of riboflavin into the inside of the plastic bottle B without being influenced by lactose input at the same time.

Thus, in this first embodiment, the microorganism contamination inspection system which can instantaneously inspect microorganism contamination of the container in which pharmaceuticals are filled or accommodated for individual containers can be provided.

Second Embodiment

Figure 8:
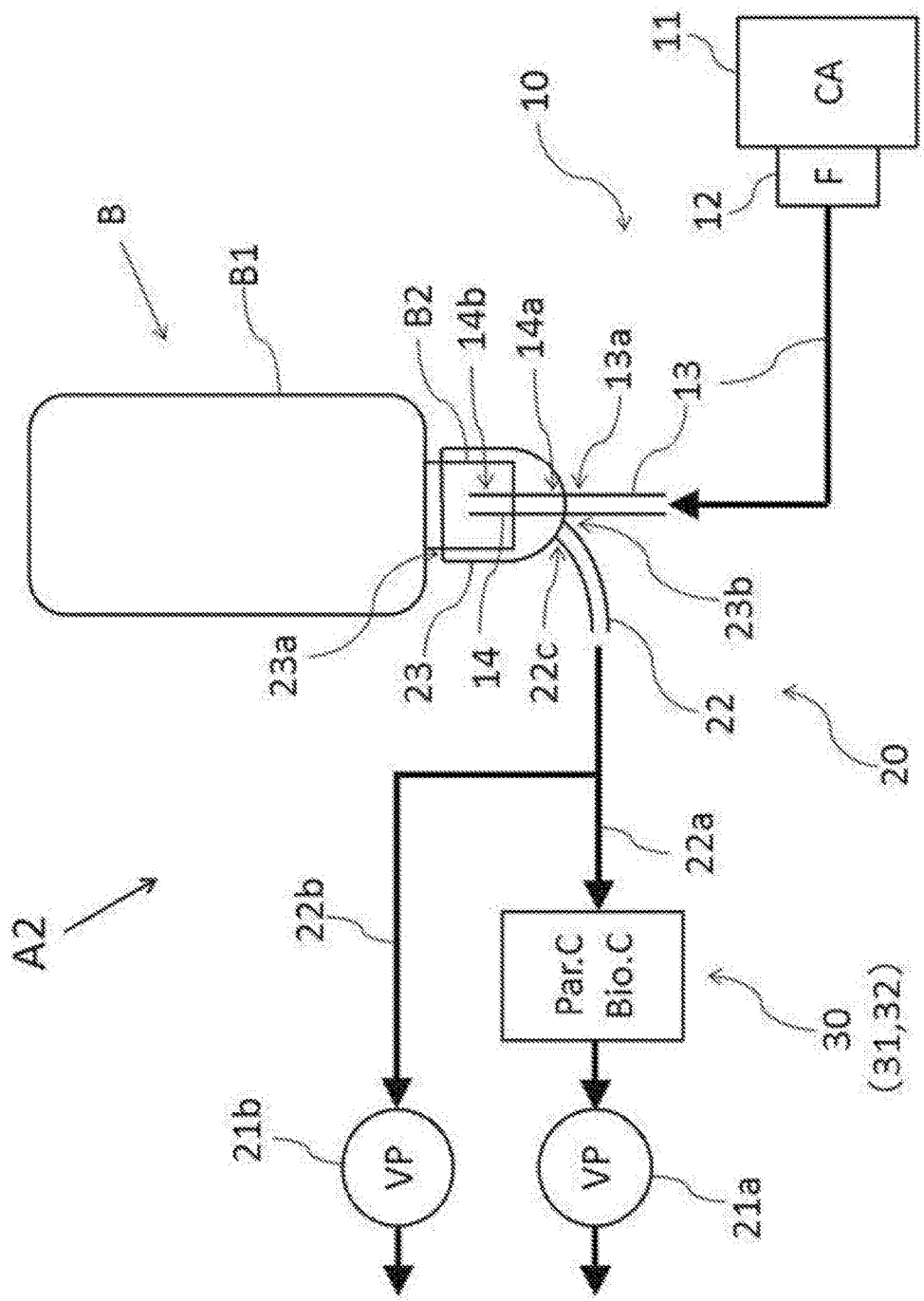
FIG. 8 is a schematic diagram illustrating configuration of a microorganism contamination inspection system according to a second embodiment.

In this second embodiment, the plastic bottle having a capacity of 150 ml similarly to the aforementioned first embodiment is used. FIG. 8 is a schematic diagram illustrating configuration of the microorganism contamination inspection system according to this second embodiment. FIG. 8 illustrates a state where the plastic bottle which is an inspection target is attached to the microorganism contamination inspection system. Moreover, though not shown, the microorganism contamination inspection system in FIG. 8 is accommodated inside a clean room, a RABS (Restricted Access Barrier System) or an isolator under an environment at Grade A.

As illustrated in FIG. 8, the microorganism contamination inspection system A2 according to this second embodiment has the same configuration as the microorganism contamination inspection system A1 according to the aforementioned first embodiment and has the supply device 10, the collecting device 20, and the detecting device 30. In this second embodiment, the plastic bottle B is attached to the microorganism contamination inspection system A2 in an inverted state (a state where the mouth portion B2 is open downward) as illustrated in FIG. 8.

In FIG. 8, each configuration of the supply device 10, the collecting device 20, and the detecting device 30 is similar to that in the microorganism contamination inspection system A1 according to the aforementioned first embodiment, and the detecting device 30 includes the particle counter 31 and the floating bacteria counter 32. These counters 31 and 32 suction the certain amount of the inspection air sent from the suctioning pipeline 22 from a collection port as a sample and can instantaneously detect the total number of the microorganism particles and the non-microorganism particles in the inspection air and the number of microorganism particles.

Moreover, since an operation of the microorganism contamination inspection system A2 according to this second embodiment can be carried out similarly to the aforementioned first embodiment, the microorganism contamination inspection system which can instantaneously inspect microorganism contamination of the container in which pharmaceuticals are filled or accommodated for individual containers even if the plastic bottle B is in the inverted state.

Third Embodiment

Figure 9:
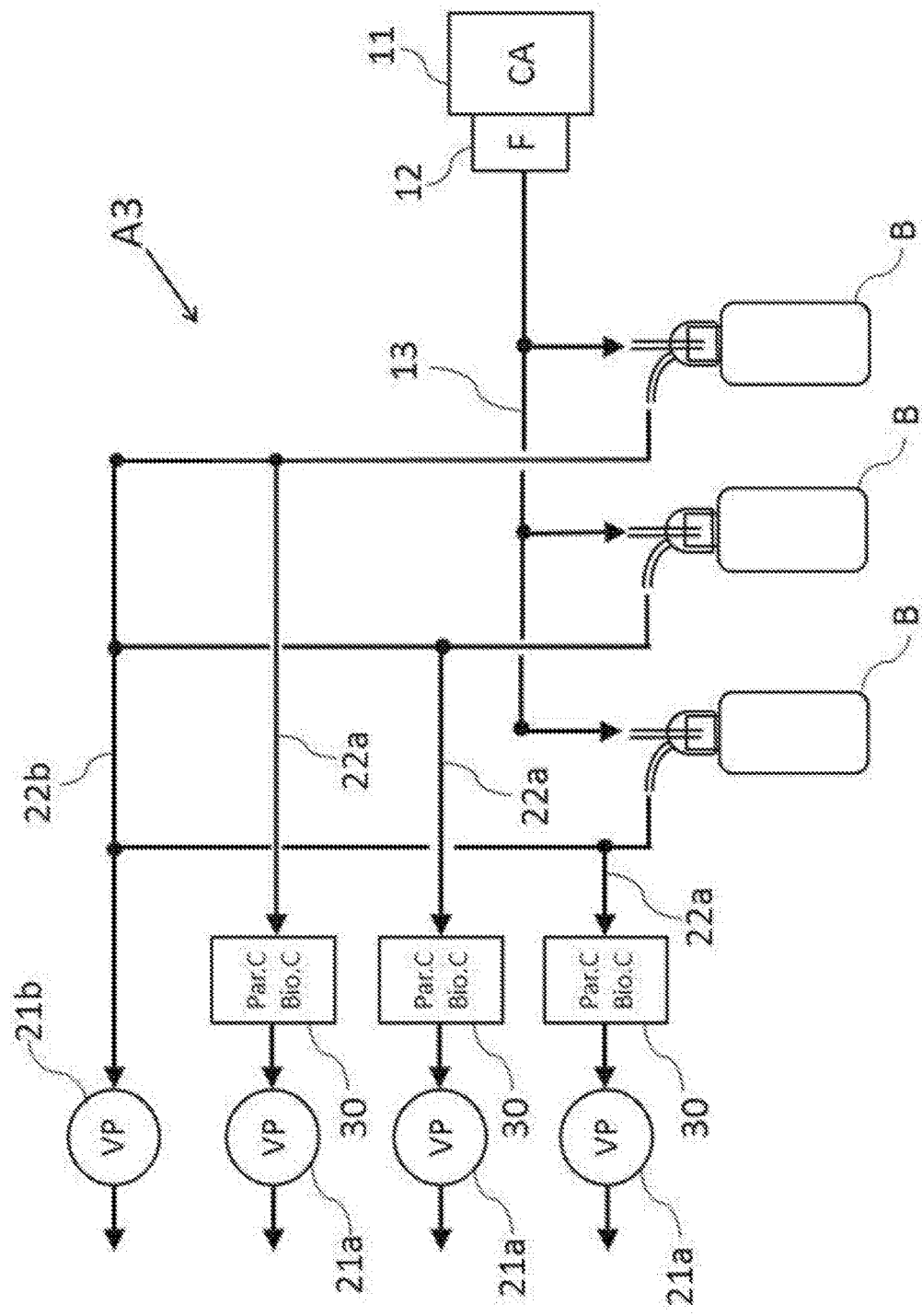
FIG. 9 is a schematic diagram illustrating configuration of a microorganism contamination inspection system according to a third embodiment.

In this third embodiment, a plurality of plastic bottles each having a capacity of 150 ml similarly to the aforementioned first embodiment is inspected at the same time. FIG. 9 is a schematic diagram illustrating configuration of the microorganism contamination inspection system according to this third embodiment. FIG. 9 illustrates a state where the plastic bottle which is an inspection target is attached to the microorganism contamination inspection system. Moreover, though not shown, the microorganism contamination inspection system in FIG. 9 is accommodated inside a clean room, a RABS (Restricted Access Barrier System) or an isolator under an environment at Grade A.

As illustrated in FIG. 9, with regard to the microorganism contamination inspection system A3 according to this third embodiment, three units of the detecting device 30 of the microorganism contamination inspection system A1 according to the aforementioned first embodiment are configured in parallel so that three plastic bottles can be inspected at the same time. In this third embodiment, the three plastic bottles B are attached to the microorganism contamination inspection system A3 in parallel in an upright state (a state where the mouth portion B2 is open upward) as illustrated in FIG. 9.

In FIG. 9, the clean air (compressed air) supplied from one unit of the compressor 11 and the sterile filter 12 is supplied from three ejection nozzles 14 through three systems of the supply pipelines 13 to the three plastic bottles, respectively. Subsequently, the inspection air collected from the three collectors 23 is supplied to the three units of the detecting devices 30 through three systems of the suctioning pipelines 22a, respectively. The three units of the detecting devices 30 can instantaneously and simultaneously detect the total number of microorganism particles and non-microorganism particles and the number of microorganism particles in the inspection air supplied from each of the plastic bottles B, respectively.

Moreover, since the microorganism contamination inspection system A3 according to this third embodiment can conduct microorganism contamination inspection of a plurality of containers (not limited to three pieces) separately and simultaneously, productivity (processing efficiency) of the inspection is drastically improved. Therefore, even if the microorganism contamination inspection process is included inline in the pharmaceutical filling process, the productivity of the filling process is not influenced. Thus, the microorganism contamination inspection system which can instantaneously and highly efficiently inspect the microorganism contamination of the containers in which the pharmaceuticals are filled or accommodated for individual containers can be provided.

Fourth Embodiment

Figure 10:
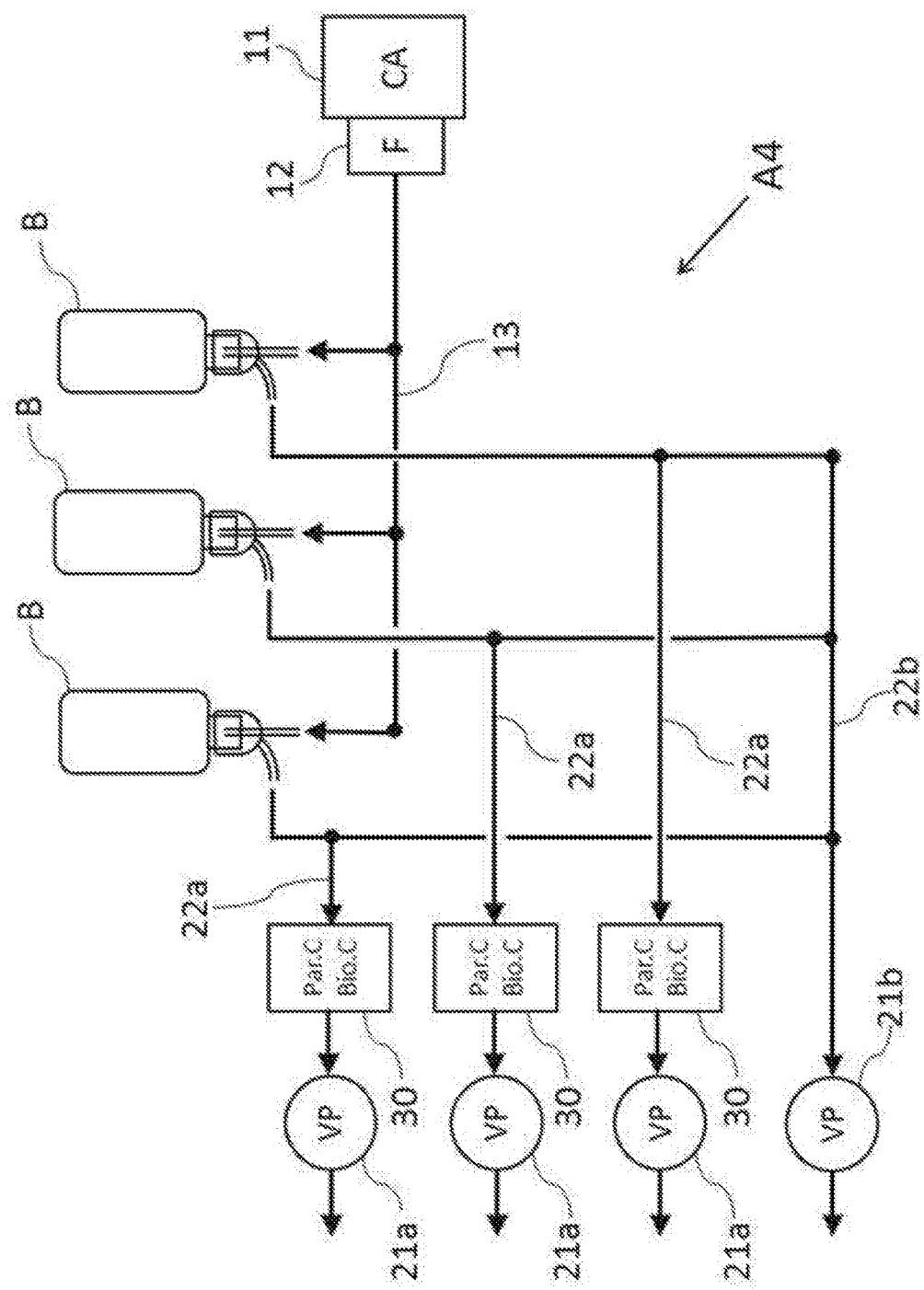
FIG. 10 is a schematic diagram illustrating configuration of a microorganism contamination inspection system according to a fourth embodiment.

In this fourth embodiment, a plurality of plastic bottles B, each having a capacity of 150 ml similarly to the aforementioned second embodiment is inspected at the same time. FIG. 10 is a schematic diagram illustrating configuration of the microorganism contamination inspection system according to this fourth embodiment. FIG. 10 illustrates a state where the plastic bottle which is an inspection target is attached to the microorganism contamination inspection system. Moreover, though not shown, the microorganism contamination inspection system in FIG. 10 is accommodated inside a clean room, a RABS (Restricted Access Barrier System) or an isolator under an environment at Grade A.

As illustrated in FIG. 10, with regard to the microorganism contamination inspection system A4 according to this fourth embodiment, three units of the detecting device 30 of the microorganism contamination inspection system A2 according to the aforementioned second embodiment are configured in parallel so that three plastic bottles can be inspected at the same time. In this fourth embodiment, the three plastic bottles B are attached in parallel to the microorganism contamination inspection system A4 in the inverted state (the state where the mouth portion B2 is open downward) as illustrated in FIG. 10.

In FIG. 10, the clean air (compressed air) supplied from one unit of the compressor 11 and the sterile filter 12 is supplied from three ejection nozzles 14 through three systems of the supply pipelines 13 to the three plastic bottles, respectively. Subsequently, the inspection air collected from the three collectors 23 is supplied to the three units of the detecting devices 30 through three systems of the suctioning pipelines 22a, respectively. The three units of the detecting devices 30 can instantaneously and simultaneously detect the total number of microorganism particles and non-microorganism particles and the number of microorganism particles in the inspection air supplied from each of the plastic bottles B, respectively.

Moreover, since the microorganism contamination inspection system A4 according to this fourth embodiment can conduct microorganism contamination inspection of a plurality of containers (not limited to three pieces) separately and simultaneously, productivity (processing efficiency) of the inspection is drastically improved. Therefore, even if the microorganism contamination inspection process is included inline in the pharmaceutical filling process, the productivity of the filling process is not influenced. Thus, the microorganism contamination inspection system which can instantaneously and highly efficiently inspect the microorganism contamination of the containers in which the pharmaceuticals are filled or accommodated for individual containers can be provided.

As described above, by utilizing the microorganism contamination inspection system according to the present invention, the plastic bottle having a concern of internal microorganism contamination can be rationally eliminated for the low F0 sterile formulation using the mass-produced plastic bottles, and sterility of the low F0 sterile formulation can be ensured high. The microorganism contamination inspection system according to the present invention can be utilized by being included inline in the pharmaceutical filling line in the actual pharmaceutical filling process. In this case, the plastic bottle for which microorganism contamination was checked can be discarded before or after filling of the pharmaceuticals so as not to be shipped.

In practicing the present invention, not only to each of the aforementioned embodiments, the following various variations can be cited:

(1) In each of the aforementioned embodiments, a plastic bottle having a capacity of 150 ml is used as a container to be inspected, but this is not limiting, and a capacity of the plastic bottle may be anything, and other containers such as a glass bottle, a can, a soft bag, a petri dish, a tray, and a film other than the plastic bottle may be used as targets.

(2) In each of the aforementioned embodiments, microorganism contamination inside the container is inspected, but this is not limiting, and an inner surface (a surface to be used) of a container, a petri dish, a tray or the like may be inspected.

(3) In each of the aforementioned embodiments, the particle counter and the floating bacteria counter are both used as the detecting devices, but this is not limiting, and only either one of the particle counter and the floating bacteria counter may be used.

(4) In each of the aforementioned embodiment, two units of the suctioning pumps are used, that is, the suctioning pump for supplying the inspection air to the detecting device and the suctioning pump carrying out main air-discharge, separately, but this is not limiting, and piping may be laid such that one unit of the suctioning pump serves the both.

(5) In each of the aforementioned embodiments, an automatic operation of the microorganism contamination inspection system was not described, but continuous running of the container and the microorganism contamination inspection may be automated by control using a microcomputer.

(6) In the aforementioned third and fourth embodiments, the three units of the detecting devices are configured in parallel so that microorganism contamination inspection for the three containers is conducted at the same time, but this is not limiting, and it may be configured such that further more containers can be inspected at the same time.

(7) In the aforementioned third and fourth embodiments, separate suctioning pumps (three units, for example) are used for a plurality (three units, for example) of the detecting devices, respectively, but this is not limiting, and piping may be laid such that one unit of the suctioning pump serves for the plurality (three units, for example) of the detecting devices.

(8) In each of the aforementioned embodiments, it is proposed that the microorganism contamination inspection system according to the present invention is included inline in the pharmaceutical filling line, but this is not limiting, and it may be employed as a line separate from the pharmaceutical filling line or may be employed in a container manufacturing process, a receiving process after conveyance of the container or a storage process before use of the container.

REFERENCE SIGNS LIST

A1, A2, A3, A4: microorganism contamination inspection system,
B: plastic bottle, B1: body portion, B2: mouth portion,
X1 to X4: plastic bottle of check test,
X1a to X4a: detection peak of particles (riboflavin and lactose)
X2b to X4b: detection peak of simulated floating bacteria (riboflavin)
10: supply device, 11: compressor, 12: sterile filter,
13: supply pipeline, 14: ejection nozzle,
20: collecting device, 21a, 21b: suctioning pump,
22 (22a, 22b): suctioning pipeline, 23: collector,
30: detecting device, 31: particle counter, 32: floating bacteria counter.

The invention claimed is:

1. A microorganism contamination inspection system for inspecting microorganism contamination of an inside or on a surface of a container, comprising:
(a) supply means for supplying a first predetermined amount of clean air to the inside or the surface of the container, the supply means including:
an air-compressor configured to deliver compressed air to an outlet of the compressor;
a sterile filter disposed at the outlet of the compressor to receive the compressed air and to transmit clean compressed air directly to a clean air supply line;
the clean air supply line located to accept the clean compressed air from the sterile filter and to deliver the clean compressed air directly to an ejection nozzle terminating said clean air supply line and through the ejection nozzle directly to the container; and
the ejection nozzle having a nozzle outlet that, in operation of the system, is either inserted into a mouth of the container or disposed at a location at the surface of the container;
(b) collecting means for collecting a second predetermined amount of air from the container, the collecting means including:
a collector unit dimensioned as a shell having an internal volume and an opening, the opening providing fluid access to the internal volume,
wherein, in operation of the system, the opening is positioned to cover either said mouth of the container or said location at the surface of the container, and
wherein the ejection nozzle passes through the shell and through the opening;
a main suction pipeline having a first end and a second end, wherein the first end is directly connected to the internal volume, wherein the second end is directly connected to a first suction pump; and
the first suction pump separated from the shell and the internal volume of the collector unit by the main inspection supply line and configured to generate suction to intake the second predetermined amount of air from the container and through the volume into the main suction pipeline; and
(c) detecting means for detecting a microorganism contained in the second predetermined amount of air,
wherein said detecting means is disposed at the main suction pipeline between the first and second ends to separate the first pump from the collector unit and to receive a portion of the second predetermined amount of air from the container through the internal volume of the collector unit into the main suction pipeline during an operation of the first pump.

2. The microorganism contamination inspection system according to claim 1, wherein the supply means is configured to eject the clean compressed air from the ejection nozzle to the inside of the container or the location at the surface of the container at an ejection pressure from 0.1 MPa to 1.0 MPa and to deliver said clean compressed air to the inside of the container or the location at the surface of the container at a rate from 0.1 L/min to 1.0 L/min.

3. The microorganism contamination inspection system according to claim 1 or 2, wherein
the detecting means has a microorganism detection portion configured to detect a number of microorganism particles in said portion of the second predetermined amount of air instantaneously.

4. The microorganism contamination inspection system according to claim 1 or 2, wherein
the detecting means has a particle detection portion and a microorganism detection portion and is configured to detect a number of microorganism particles instantaneously by simultaneously
(4a) discriminating the microorganism particles from non-microorganism particles contained in the portion of the second predetermined amount of air, and
(4b) instantaneously detecting a total number of the microorganism particles and the non-microorganism particles, contained in the portion of the second predetermined amount of air, in the particle detection portion; and
(4c) instantaneously detecting the number of microorganism particles, contained in the portion of the second predetermined amount of air, in the microorganism detection portion.

5. The microorganism contamination inspection system according to claim 3, wherein
the microorganism contamination detection portion is configured to instantaneously detect a number of microorganism particles in the portion of the second predetermined amount of air with a use of a laser induced fluorescence.

6. The microorganism contamination inspection system according to claim 4, wherein
the microorganism contamination detection portion is configured to instantaneously detect a number of microorganism particles in the portion of the second predetermined amount of air with a use of a laser induced fluorescence.

7. The microorganism contamination inspection system according to claim 1, further comprising
a second suction pump;
a branch suction pipeline having third and fourth ends, wherein the third end is fluidly connected to the main suction pipeline between the first end and the detection means, wherein the fourth end is directly connected to the second suction pump.

8. The microorganism contamination inspection system according to claim 7, wherein the second suction pump is configured to operate only when the air-compressor is operated.

9. The microorganism contamination inspection system according to claim 1, configured such that the first predetermined amount of air is equal to the second predetermined amount of air to prevent leakage of contaminant from the container to surrounding environment.

* * * * *